US006462226B1

(12) United States Patent
Mair

(10) Patent No.: US 6,462,226 B1
(45) Date of Patent: Oct. 8, 2002

(54) PROCESS FOR THE PREPARATION OF 4,5-DIAMINO SHIKIMIC ACID DERIVATIVES

(75) Inventor: Hans-Juergen Mair, Loerrach (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/715,363

(22) Filed: Nov. 17, 2000

(30) Foreign Application Priority Data

Dec. 3, 1999 (EP) .............................................. 99124223

(51) Int. Cl.$^7$ ........................ C07C 69/74; C07C 229/52
(52) U.S. Cl. ....................................... 560/128; 560/125
(58) Field of Search ................................. 560/125, 128

(56) References Cited

U.S. PATENT DOCUMENTS 5,859,284 A * 1/1999 Kent et al. .................. 560/125

FOREIGN PATENT DOCUMENTS

WO WO 96 26933 9/1996
WO WO 98/07685 2/1998

OTHER PUBLICATIONS

Rohloff et al., J. Org. Chem., vol. 63, pp. 4545–4550 (1998).
Greene et al., "Protective Groups in Organic Chemistry", John Wiley & Sons Inc., New York, pp. 315–385 (1991).
Knouzi, Noureddine, et al., Bull. Soc. Chim. Fr., No. 5, pp. 815–819 (1985).

* cited by examiner

Primary Examiner—Alan L. Rotman
Assistant Examiner—Ebenezer Sackey
(74) Attorney, Agent, or Firm—George W. Johnston; Dennis P. Tramaloni

(57) ABSTRACT

A new process for the preparation of 4,5-diamino shikimic acid derivatives starting from 4-amino-5-azido shikimic acid derivatives is provided.

4,5-diamino shikimic acid derivatives and its pharmaceutically acceptable addition salts are potent inhibitors of viral neuraminidase.

15 Claims, No Drawings

PROCESS FOR THE PREPARATION OF 4,5-DIAMINO SHIKIMIC ACID DERIVATIVES

FIELD OF THE INVENTION

The present invention relates to a process for the preparation of 4,5-diamino shikimic acid derivatives, especially for the preparation of ethyl (3R, 4R, 5S)-4-acetamido-5-amino-3-(1-ethylpropoxy)-1-cyclohexene-1-carboxylate and its pharmaceutically acceptable addition salts from 4-amino-5-azido shikimic acid derivatives, especially from ethyl (3R, 4R, 5S)-4-acetamido-5-azido-3-(1-ethylpropoxy)-1-cyclohexene-1-carboxylate.

BACKGROUND OF THE INVENTION 4,5-diamino shikimic acid derivatives, especially the ethyl (3R, 4R, 5S)-4-acetamido-5-amino-3-(1-ethylpropoxy)-1-cyclohexene-1-carboxylate and its pharmaceutically acceptable addition salts are potent inhibitors of viral neuraminidase (J. C. Rohloff et al., J.Org.Chem. 63, 1998, 4545–4550; WO 98/07685).

A reduction of ethyl (3R, 4R, 5S)-4-acetamido-5-azido-3-(1-ethylpropoxy)-1-cyclohexene-1-carboxylate to ethyl (3R, 4R, 5S)-4-acetamido-5-amino-3-(1-ethylpropoxy)-1-cyclohexene-1-carboxylate by a hydrogenation in the presence of a Raney nickel catalyst is known in the art (J. C. Rohloffet al, loc.cit.).

It was found that the "5-azido" starting compound from its prior synthesis always contains a small amount of the "2,5-diazido" compound formed by formal addition of hydrazoic acid to the double bond. In the course of the hydrogenation the azido group in 5-position is readily converted to the desired amino group, the transformation of the azido group in 2-position however is very slow. Accordingly a "2-azido-5-amino" intermediate is formed which was shown to be "Ames positive" and therefore suspicious of being mutagenic.

This intermediate cannot be satisfactorily removed with the common purification techniques. Also, the problem cannot be overcome by prolonging the hydrogenation time because the "cyclohexene double bond" becomes hydrogenated, too.

An object of the present invention is, therefore, to provide a process for the preparation of 4,5-diamino shikimic acid derivatives which does not encompass the difficulties known in the art; i.e. a process which allows easy access to the target product in an excellent quality.

DESCRIPTION OF THE INVENTION

It was found that reduction of 4-amino-5-azido shikimic acid derivatives with a phosphine in the presence of a carboxylic acid surprisingly achieved this object.

The present invention therefore relates to a process for the preparation of a 4,5-diamino shikimic acid derivative of formula

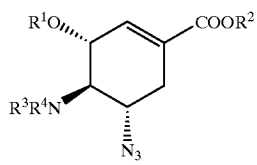

and a pharmaceutically acceptable addition salt thereof wherein $R^1$ is an optionally substituted alkyl group,
$R^2$ is an alkyl group and
$R^3$ and $R^4$, independent of each other are H or an amino protecting group, with the proviso that not both $R^3$ and $R^4$ are H;
the process being characterized by the reduction of a 4-amino-5-azido-shikimic acid derivative of formula

II with a phosphine in the presence of a carboxylic acid. $R^1$, $R^2$, $R^3$ and $R^4$ have the same meaning in formula II as in formula I. If necessary, the process includes a further transformation of the 4,5-diamino shikimic acid derivative into a pharmaceutically acceptable addition salt thereof.

The term alkyl in $R^1$ has the meaning of a straight chained or branched alkyl group of 1 to 20 C-atoms, expediently of 1 to 12 C-atoms. Examples of such alkyl groups are methyl, ethyl, n-propyl, i-propyl, n-butyl, i-butyl, tert. butyl, pentyl and its isomers, hexyl and its isomers, heptyl and its isomers, octyl and its isomers, nonyl and its isomers, decyl and its isomers, undecyl and its isomers and dodecyl and its isomers.

This $R^1$ alkyl group can be substituted with one or more substituents as defined in e.g. WO 98/07685. Suitable substituents are $C_{1-6}$-alkyl (as defined above), $C_{1-6}$-alkenyl, $C_{3-6}$-cycloalkyl, hydroxy, $C_{1-6}$-alkoxy, $C_{1-6}$-alkoxycarbonyl, F, Cl, Br, and I. Preferred meaning for $R^1$ is 1-ethylpropyl.

$R^2$ is a straight chained or branched alkyl group of 1 to 12 C-atoms, expediently of 1 to 6 C-atoms as exemplified above.

The preferred meaning for $R^2$ is ethyl.

The term amino protecting group in $R^3$ and $R^4$ refers to any protecting group conventionally used and known in the art. They are described e.g. in "Protective Groups in Organic Chemistry", Theodora W. Greene et al., John Wiley & Sons Inc., New York, 1991, p.315–385. Suitable amino protecting groups are also given in e.g. WO 98/07685.

Preferred amino protecting groups are alkanoyl groups, more preferably lower $C_{1-6}$-alkanoyl such as hexanoyl, pentanoyl, butanoyl (butyryl), propanoyl (propionyl), ethanoyl (acetyl) and methanoyl (formyl). The preferred alkanoyl group, and therefore preferred meaning for $R^4$, is acetyl. The preferred meaning for $R^4$ is H.

The 4-amino-5-azido-shikimic acid derivative of formula (II) as starting compounds of the present process of the invention are accessible as described in J. C. Rohloff et al., loc. cit. and in WO 98/07685.

The preferred 4-amino-5-azido-shikimic acid derivative of formula (II) is the ethyl (3R, 4R, 5S)-4-acetamido-5-azido-3-(1-ethylpropoxy)-1-cyclohexene-1-carboxylate. Accordingly, the preferred 4,5-diamino shikimic acid derivative of formula (I) is the ethyl (3R, 4R, 5S)-4-acetamido-5-amino-3-(1-ethylpropoxy)-1-cyclohexene-1-carboxylate and the corresponding salt, ethyl (3R, 4R, 5S)-4-acetamido-5-amino-3-(1-ethylpropoxy)-1-cyclohexene-1-carboxylate Phosphate (1:1).

The phosphine used can be defined by the formula

III wherein $R^5$ is alkyl.

$R^5$ expediently is a straight chained or branched $C_{1-8}$ alkyl group as defined above.

Phosphines which can suitably be used are trioctyl phosphine, triisobutyl phosphine, tri-n-butyl phosphine, and triethyl phosphine. The most preferred phosphine is tri-n-butyl phosphine.

Although the ratio of phospine to the 4-amino-5-azido-shikimic acid derivative of formula (II) is not critical to the production of the desired 4,5-diamino shikimic acid derivative of formula (I), the phosphine is preferably added in stoichiometric amounts or in a slight excess of up to 1.05 equivalents relating to the starting amount of the 4-amino-5-azido-shikimic acid derivative of formula (II). One of skill in the art may adjust to relative amounts of phosphine and the 4-amino-5-azido-shikimic acid derivative of formula (II) to optimize them for the particular reaction conditions used.

Typically, the reduction is performed in a polar protic solvent which forms the reaction medium. Any conventional polar protic solvent can be used, such as alcohols, preferably aqueous ethanol or aqueous tetrahydrofuran, most preferably aqueous ethanol. However, the choice of solvent is not critical to production of the desired 4,5-diamino shikimic acid derivative of formula (I), and one of skill would be able to perform the reduction in other solvents using general knowledge of the art.

The reaction temperature is another non-critical variable; for instance, the reduction performs satisfactorily at room temperature. The preferred reaction temperature mainly depends on the phosphine used but most preferably lies in the range of −20° C. to 30° C., with between 0 and 25° C. being particularly preferred.

It can be favorable to perform the reaction at two temperature levels, thereby having the lower temperature range given above for the addition of the phosphine and thereafter having a slightly higher temperature of up to room temperature to bring the reaction to completion.

Catalytic amounts of a carboxylic acid present during the reduction were found to suppress the ester hydrolysis which otherwise takes place to a small extent of some percent and thereby leads to an undesirable impurity. The term "carboxylic acid" refers to any compound having one or more free carboxylic acid groups. Preferably, the carboxylic acid is an aliphatic carboxylic acid, having from 2 to 8 carbon atoms, such as acetic acid, oxalic acid, propionic acid, malonic acid, butyric acid, succinic acid, maleic acid, fumaric acid, valeric acid, glutaric acid, caproic acid, adipic acid, heptanoic acid, and caprylic acid.

The carboxylic acid is preferably present in the reduction reaction in an amount which measurably reduces the quantity of ester hydrolysis products present after the reaction of a 4-amino-5-azido-shikimic acid derivative of formula (II) with a phosphine to produce the 4,5-diamino shikimic acid derivative of formula (I). More preferably, the carboxylic acid is added to the reaction in quantities from about 0.5 to about 5.0 mol % of the starting amount of the 4-amino-5-azido-shikimic acid derivative of formula (II). Most preferably, the carboxylic acid is added to the reaction in quantities from about 0.5 to about 3.0 mol % of the starting amount of the 4-amino-5-azido-shikimic acid derivative of formula (II). Particularly preferred is the addition of carboxylic acid to the reaction in an amount of about 1.0 mol % of the starting amount of the 4-amino-5-azido-shikimic acid derivative of formula (II).

Preferably, one of skill in the art will be able to adjust the amount of a particular carboxylic acid added to the reaction according to the number of free carboxylic acid groups and the pKa value of the particular acid. Higher pKa acids will be required in relatively larger amounts than lower pKa acids.

Expediently, acetic acid, usually in the form of glacial acetic acid, is added in catalytic quantities of 0.5 mol % to 3.0 mol % of the 4-amino-5-azido-shikimic acid derivative of formula (II).

Although the time allowed for the reaction is not critical, generally, the reduction reaction is complete after 3 to 6 hours.

Thereafter work up of the reaction mixture can happen by applying methods known to those skilled in the art. Expediently the reaction mixture is, preferably after stabilization with ≦5 mol % acetic acid, concentrated in vacuo.

Though the 4,5-diamino shikimic acid derivative can be isolated e.g. by evaporation and crystallization, it is preferably kept in e.g. an ethanolic solution and then further transformed into the pharmaceutically acceptable addition salt following the methods described in J. C. Rohloff et al., J.Org.Chem. 63, 1998, 4545–4550; WO 98/07685).

The term "pharmaceutically acceptable acid addition salts" embraces all conventionally used salts for pharmaceutical preparations, including salts with inorganic and organic acids, such as hydrochloric acid, hydrobromic acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

The salt formation is effected with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

Preferred pharmaceutically acceptable acid addition salt is the 1:1 salt with phosphoric acid which can be formed preferably in ethanolic solution at a temperature of −20° C. to 60° C.

The following examples shall illustrate the invention in more detail without limiting it.

1. Preparation of Ethyl (3R, 4R, 5S)-4-acetamido-5-amino-3-(1-ethylpropoxy)-1-cyclohexene-1-carboxylate 50.0 g (0.147 mol ) ethyl (3R, 4R, 5S)-4-acetamido-5-azido-3-(1-ethylpropoxy)-1-cyclohexene-1-carboxylate were placed in a nitrogen purged 1000 ml glass reactor fitted with a mechanical stirrer, a condenser, and a 250 ml dropping funnel. 300 ml ethanol, 50 ml water and 0.09 g acetic acid were added. To the resulting clear solution 31.4 g (0.155 mol) tributylphosphine dissolved in 150 ml ethanol were continuously added at a temperature of 5° C. (+/−5° C.) over a period of 30–90 min. Under slight cooling of the jacket (~3° C.) the reaction temperature was kept at this temperature. The feeder was rinsed with 20 ml ethanol. The clear reaction mixture was stirred for additional 90 min at 5° C. (+/−5° C.) under slight jacket cooling. Subsequently the temperature was raised within 30–60 min to 20–25° C. and the solution was stirred for another 3 h (nitrogen evolving).

After the reaction was finished (HPLC control) 0.18 g acetic acid were added to the clear solution. Then the mixture was concentrated under reduced pressure (300 to 50 mbar) at a maximum temperature of 60° C. and a maximum jacket temperature of 75° C. near to dryness. The oily residue (80–100 ml) was diluted with 160 ml ethanol, the resulting solution was then again concentrated following the method as mentioned above. The oily residue was dissolved in ethanol up to a volume of 250 ml. The water content of this solution was determined by K F (Karl Fischer) titration of being less than 1.0% wt. %. Yield: 44.4 g (97% area by HPLC) of the title product in ethanolic solution.

2. Preparation of Ethyl (3R, 4R, 5S)-4-acetamido-5-amino-3-(1-ethylpropoxy)-1-cyclohexene-1-carboxylate Phosphate (1:1)

In a dry and nitrogen purged 1000 ml glass reactor fitted with a mechanical stirrer, a condenser, and a 500 ml dropping funnel 17.0 g ortho phosphoric acid (85% in water) were dissolved in 400 ml ethanol and the resulting clear solution was warmed to 50–55° C. Subsequently the 250 ml ethanolic solution obtained from example 1 and containing 0.147 mol of ethyl (3R, 4R, 5S)-4-acetamido-5-amino-3-(1-ethylpropoxy)-1-cyclohexene-1-carboxylate were added under stirring. After fast addition (10–15 min) of two thirds (ca.160 ml) of the total volume of this solution the addition was stopped and the supersaturated clear solution was seeded with 0.2 g of previously obtained ethyl (3R, 4R, 5S)-4-acetamido-5-amino-3-(1-ethylpropoxy)-1-cyclohexene-1-carboxylate Phosphate (1:1). Immediately afterwards crystallization commenced. The resulting thick suspension was stirred for 45–60 min at 50–55° C. Then the remaining amine solution was slowly added (45–60 min) to the suspension at 50–55° C. The feeder was rinsed with 20 ml ethanol. Subsequently the thick suspension was continuously cooled to 12–20° C. in about 4 h (cooling speed=10° C./h). To complete the crystallization stirring was continued at 12–20° C. for additional 2±1 h. Ethyl (3R, 4R, 5S)-4-acetamido-5-amino-3-(1-ethylpropoxy)-1-cyclohexene-1-carboxylate Phosphate (1:1) was isolated by pressure filtration (0.3 bar nitrogen overpressure, Dacron® filter cloth). The crystalline product was washed twice with 240 ml acetone and twice with 300 ml n-heptane at room temperature. Ethyl (3R, 4R, 5S)-4-acetamido-5-amino-3-(1-ethylpropoxy)-1-cyclohexene-1-carboxylate Phosphate (1:1) was dried in vacuo (≈20 mbar) at a maximum temperature of 50° C. until constant weight.

Yield: 54–55 g (88–91%) of the title product in the form of colorless needles with an assay of 99 wt. % (sum of impurities <0.5 wt. %, single impurities ≦0.1 wt. %).

COMPARISON EXAMPLE 1

Preparation of Ethyl (3R, 4R, 5S)-4-acetamido-5-amino-3-(1-ethylpropoxy)-1-cyclohexene-1-carboxylate (Hydrogenation with Ra-Ni)

100 g (0.295 mol) ethyl (3R, 4R, 5S)-4-acetamido-5-azido-3-(1-ethylpropoxy)-1-cyclohexene-1-carboxylate were dissolved in 800 ml ethanol and placed in a 21 steel autoclave together with 34 g Raney Nickel (Degussa) in 200 ml ethanol. The autoclave was closed rinsed twice with nitrogen and then set under 2 bar hydrogen pressure. Hydrogenation took place at a temperature of 20–25° C. under mechanical stirring a 1000 rpm until, after all the starting material had reacted, also the content of the "2-azido-5-amino intermediate" was ≦0.01% area (GC measurement) which was about 5–8 h. However, it was found that due to this "overhydrogenation" the "cyclohexene double bond" became hydrogenated, too.

The content of the respective cyclohexane derivative accordingly was 3–6% area (GC measurement).

Work up was performed by addition of 52 ml Cyclopentene and 1 h subsequent stirring in a nitrogen atmosphere. The reaction mixture was then pressed through a pressure filter (2 bar $N_2$ overpressure). The residue in the reactor was was then diluted with 400 ml ethanol followed by pressure filtration. The combined filtrates (ca. 1250 ml) were concentrated to 500 ml solution and contained about 70–80 g of the title product.

COMPARISON EXAMPLE 2

Preparation of Ethyl (3R, 4R, 5S)-4-acetamido-5-amino-3-(1-ethylpropoxy)-1-cyclohexene-1-carboxylate Phosphate (1:1)

In a dry and nitrogen purged 2000 ml glass reactor fitted with a mechanical stirrer, a condenser, and a 500 ml dropping funnel 33.0 g ortho phosphoric acid (85% in water) were dissolved in 1400 ml ethanol and the resulting clear solution was warmed to 50–55° C. Subsequently the 500 ml ethanolic solution obtained from comparison example 1 and containing about 224 mmol of ethyl (3R, 4R, 5S)-4-acetamido-5-amino-3-(1-ethylpropoxy)-1-cyclohexene-1-carboxylate were added under stirring. After fast addition (10–15 min) of two thirds (ca.330 ml) of the total volume of this solution the addition was stopped and the supersaturated clear solution was seeded with 0.4 g of previously obtained ethyl (3R, 4R, 5S)-4-acetamido-5-amino-3-(1-ethylpropoxy)-1-cyclohexene-1-carboxylate Phosphate (1:1). Immediately afterwards crystallization commenced. The resulting thick suspension was stirred for 45–60 min at 50–55° C. Then the remaining amine solution was slowly added (45–60 min) to the suspension at 50–55° C. The feeder was rinsed with 20 ml ethanol. Subsequently the thick suspension was continuously cooled to −20° C. in about 6 to 7 h. To complete the crystallization stirring was continued at −20° C. Ethyl (3R, 4R, 5S)-4-acetamido-5-amino-3-(1-ethylpropoxy)-1-cyclohexene-1-carboxylate Phosphate (1:1) was isolated by filtration and washed twice with 480 ml of acetone (room temperature). The crystalline product was resuspended in 2600 ml acetone for 3 h at 24° C. to 28° C., filtrated, washed twice with 400 ml acetone (room temperature) and twice with 600 ml n-heptane (room temperature). Ethyl (3R, 4R, 5S)-4-acetamido-5-amino-3-(1-ethylpropoxy)-1-cyclohexene-1-carboxylate Phosphate (1:1) was dried in vacuo (≈20 mbar) at a temperature of 25°–28° C. until constant weight.

Yield: 73–90 g (80–85%) of the title product in the form of colorless needles with an assay of 99 wt. %. The content of the "overhydrogenated" cyclohexane derivative still was between 0.5 and 2.0 area % (GC measurement).

What is claimed is:

1. A process for the preparation of a 4,5-diamino shikimic acid derivative of formula I,

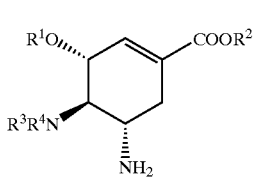

comprising reducing a 4-amino-5-azido-shikimic acid derivative of formula II

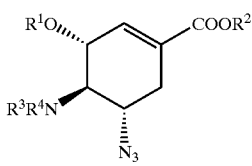

with a phosphine in the presence of a carboxylic acid to form said 4,5-diamino shikimic acid derivative of formula I wherein $R^1$ is a substituted or unsubstituted alkyl group of 1 to 20 carbon atoms, $R^2$ is an unsubstituted alkyl group of 1 to 12 carbon atoms, $R^3$ is H or an amino protecting group, and $R^4$ is an amino protecting group.

2. The process according to claim 1, wherein the carboxylic acid is an aliphatic carboxylic acid.

3. The process according to claim 2, wherein the carboxylic acid is present in an amount from about 0.5 mol % to about 5 mol % based on the 4-amino-5-azido-shikimic acid derivative of formula II to be reduced.

4. The process according to claim 3, wherein the carboxylic acid is present in an amount from about 0.5 mol % to 3 mol % based on the 4-amino-5-azido-shikimic acid derivative of formula II to be reduced.

5. The process according to claim 2, wherein the aliphatic carboxylic acid has from 2 to 8 carbon atoms.

6. The process according to claim 5, wherein the carboxylic acid is acetic acid.

7. The process according to claim 1, wherein the phosphine is a phosphine according to formula III, $$P(R^5)_3 \qquad \text{III}$$

wherein $R^5$ is an alkyl group of 1 to 8 carbon atoms.

8. The process according to claim 7, wherein the phosphine is selected from the group consisting of trioctyl phosphine, triisobutyl phosphine, tri-n-butyl phosphine and triethyl phosphine.

9. The process according to claim 8, wherein the phosphine is tri-n-butyl phosphine.

10. The process according to claim 1, wherein the reducing takes place in a polar protic solvent at a temperature of from about −20° C. to about 30° C.

11. The process according to claim 10, wherein the polar protic solvent is aqueous ethanol or aqueous tetrahydrofuran.

12. The process according to claim 1, wherein the 4,5-diamino-shikimic acid derivative of formula (I) is ethyl (3R, 4R, 5S)-4-acetamido-5-amino-3-(1-ethylpropoxy)-1-cyclohexene-1-carboxylate and the 4-amino-5-azido-shikimic acid derivative of formula (II) is ethyl (3R, 4R, 5S)-4-acetamido-5-azido-3-(1-ethylpropoxy)-1-cyclohexene-1-carboxylate.

13. A process for the preparation of a pharmaceutically acceptable addition salt of a 4,5-diamino shikimic acid derivative of formula I,

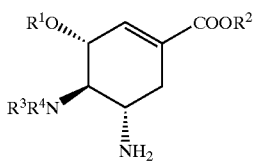

wherein $R^1$ is a substituted or unsubstituted alkyl group of 1 to 20 carbon atoms, $R^2$ is an alkyl group of 1 to 12 carbon atoms, $R^3$ is H or an amino protecting group and $R^4$ is an amino protecting group comprising:

reducing a 4-amino-5-azido-shikimic acid derivative of formula II

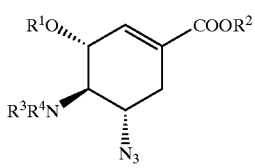

with a phosphine in the presence of a carboxylic acid to form said 4,5-diamino shikimic acid derivative of formula I, and forming a salt from said 4,5-diamino shikimic acid derivative of formula I with a pharmaceutically acceptable organic or inorganic acid.

14. The process according to claim 13, wherein the carboxylic acid is an aliphatic carboxylic acid.

15. The process according to claim 14, wherein the carboxylic acid is present in an amount from about 0.5 mol % to about 3 mol % based on the 4-amino-5-azido-shikimic acid derivative of formula II to be reduced.

* * * * *